United States Patent [19]

Bradford et al.

[11] Patent Number: Plant 7,503

[45] Date of Patent: Apr. 23, 1991

[54] PLUM TREE (PURPLE MAJESTY)

[76] Inventors: Norman G. Bradford, 11875 E. Savana Rd.; Lowell G. Bradford, 12439 E. Savana Rd., both of Le Grand, Calif. 95333

[21] Appl. No.: 457,183

[22] Filed: Dec. 26, 1989

[51] Int. Cl.[5] ..... A01H 5/00

[52] U.S. Cl. ..... Plt./38

[58] Field of Search ..... Plt./38

*Primary Examiner*—James R. Feyrer

[57] ABSTRACT

The present invention relates to a plum tree and more particularly to a new and distinct variety broadly characterized by a medium size, medium vigorous, hardy, productive, and regular bearing tree, which requires a pollinator. The fruit matures under the ecological conditions described in the latter part of June, with first picking on June 19, 1989, and is uniformly large in size, clingstone in type, very dark purplish red in skin color, smooth in surface appearance, attractive in shape, sweet in flavor, and exceptionally firm in texture, resulting in excellent quality for keeping and shipping. The variety was developed as a hybridized seedling from the selected seed parent, Red Beaut (U.S. Plant Pat. No. 2,539), and an unnamed seedling as the selected pollen parent.

1 Drawing Sheet

BACKGROUND OF THE NEW VARIETY

In a continuing effort to improve the quality of shipping fruits, we, the inventors, typically hybridize a large number of nectarine, peach, plum, apricot, and cherry seedlings each year. The present invention relates to a new and distinct variety of plum tree, which has been denominated varietally as "Purple Majesty". The present variety was hybridized by us in 1982, and the resulting seedling was planted in a cultivated area of our experimental orchard at Bradford Farms near Le Grand, Calif. in Merced County (San Joaquin Valley). Specifically, the hybridized seedling was originated by using Red Beaut (U.S. Plant Pat. No. 2,539) as the selected seed parent and an unnamed seedling as the selected pollen parent. Subsequent to origination of the present variety of plum tree, we asexually reproduced it by budding and grafting, and such reproduction of plant and fruit characteristics were true to the original plant in all respects.

The present variety produces fruit that matures at nearly the same time as Santa Rosa, unpatented, but is distinguished from that variety by being self-sterile instead of self-fertile and by producing fruit that is larger in size, firmer in texture, axially compressed in shape, and darker in skin color at shipping ripeness.

The present variety is similar to its selected seed parent, Red Beaut (U.S. Plant Pat. No. 2,539), by being self-sterile and by producing fruit that is smooth in surface appearance and very firm in texture, but is distinguished therefrom by producing fruit that ripens twenty-one days later, that is very dark reddish purple in skin color instead of red, that is much larger in size, and that is much sweeter in flavor.

DRAWING

The accompanying photograph exhibits three whole fruits positioned to display the characteristics of the skin color and form; one fruit sliced to reveal the flesh; a clean dry stone; and a branch with leaves, all typical of the subject variety.

POMOLOGICAL CHARACTERISTICS

Referring now more specifically to the pomological characteristics of this new and distinct variety of plum tree, the following has been observed under the ecological conditions prevailing at the experimental orchard of the inventors near Le Grand, Merced County (San Joaquin Valley), Calif. All major color code designations are by reference to the Inter-Society Color Council, National Bureau of Standards. Common color names are also used occasionally.

TREE

Size: Medium.
Vigor: Vigorous.
Growth: Upright and dense.
Form: Vase formed.
Hardiness: Hardy.
Production: Very productive, but requires a pollinator.
Bearing: Regular bearer.
Trunk:
- *Size.*—Medium.
- *Texture.*—Shaggy.
- *Color.*—Grayish brown [61. gy.Br].
- *Lenticels.*—Numerous. Color: Strong yellowish brown [74. s.yBr]. Average Size: ¼" [6.4 mm.].

Branches:
- *Size.*—Medium.
- *Texture.*—Medium..
- *Color.*—1st year wood — Topside: Light reddish brown [42. l.rBr]. 1st year wood — Underside: Strong yellow green [117. s.YG]. Older wood: Moderate yellowish brown [77. m.yBr].
- *Lenticels.*—Numerous, very small.

Leaves:
- *Size.*—Medium. Average length: 3⅜" [85.7 mm.]. Average width: 1½" [38.1 mm.].
- *Thickness.*—Medium.
- *Form.*—Elliptical.
- *Apex.*—Acutely pointed.
- *Base.*—Acute.
- *Surface.*—Smooth.

*Color.*—Dorsal surface: Dark olive green [126. d.01G]. Ventral surface: Moderate olive green [125. m.01G].

*Margin.*—Finely crenate.

*Venation.*—Pinnately net veined.

*Petiole.*—Average length: ⅜" [9.5 mm.]. Average thickness: 1/16" [1.6 mm.]. Dorsal side color: Brownish pink [33. brPk]. Ventral side color: Moderate yellow green [120. m.YG].

*Glands.*—Average number: 2 to 4. Position: Some oppositely and some alternately positioned on petiole and base of blade. Size: Small. Form: Globose.

*Stipules.*—Numerous. Average length: ¼" [6.4 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Medium, as compared with other varieties.

*Date of first bloom.*—Feb. 27, 1989.

*Date of full bloom.*—Mar. 9, 1989.

*Size.*—Small.

*Color.*—White [263. White].

FRUIT

Maturity when described: Firm but eating ripe, June 24, 1989.

Date of first picking: June 19, 1989.

Date of last picking: June 26, 1989.

Size: Uniform, large.

*Average diameter axially.*—2" [50.8 mm.].

*Average traversely in suture plane.*—2⅜" [60.3 mm.].

Form: Uniform, symmetrical, oblate, axially compressed.

*Longitudinal section form.*—Oblate.

*Transverse section through diameter.*—Round.

Suture: An inconspicuous line extending from the base to slightly past the apex with a slight depression beyond the pistil point.

Ventral surface: Rounded.

Lipping: Very slight if any.

Cavity: Flaring, circular, with suture showing on one side.

Base: Slightly cuneate and truncate.

Apex: Truncate.

Pistil point: An inconspicuous dot.

Stem: Medium size.

*Average length.*—½" [12.7 mm.].

*Average width.*—1/16" [1.6 mm.].

Skin:

*Thickness.*—Medium.

*Texture.*—Tough.

*Tenacity.*—Tenacious to flesh.

*Astringency.*—Strong.

*Tendency to crack.*—None observed.

*Bloom.*—Abundant (not shown in the drawing).

*Color.*—Very dark reddish purple [243. v.d.rP] with some moderate reddish brown [43. m.rBr] freckling.

Flesh:

*Color.*—Brilliant orange yellow [67. brill.OY] to the pit.

*Amygdalin.*—Scarce.

*Juice.*—Abundant, rich.

*Texture.*—Very firm, fine, very crisp.

*Fibers.*—Abundant, fine, tender.

*Ripens.*—Evenly.

*Flavor.*—Mild and very sweet.

*Aroma.*—Moderate.

*Eating quality.*—Very good.

STONE

Type: Clingstone.

Form: Oval.

Base: Straight.

Apex: Acuminate.

Sides: Equal.

Surface: Rugose, with a few characteristic ridges toward the base.

Color: Dark orange yellow [72. d.OY].

Pit wall: 1/16" [1.6 mm.] thick.

Tendency to split: None observed.

Kernel:

*Form.*—Oval.

*Taste.*—Very bitter.

*Viable.*—Yes.

*Average width.*—⅜" [9.5 mm.].

*Average length.*—½" [12.7 mm.].

Pellicle color: Dark grayish yellow [91. d.gy.Y].

Amygdalin: Abundant.

USE

Market: Fresh market, both local and long distance shipping.

Keeping quality: Excellent.

Shipping quality: Excellent.

Resistance to insects: No unusual susceptibilities noted.

Resistance to diseases: No unusual susceptibilities noted.

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, substantially as illustrated and described, which matures at nearly the same time as Santa Rosa, unpatented, but is distinguished therefrom and an improvement thereon by producing fruit that is larger in size, much firmer in texture, darker in skin color at shipping ripeness, and axially compressed in shape.

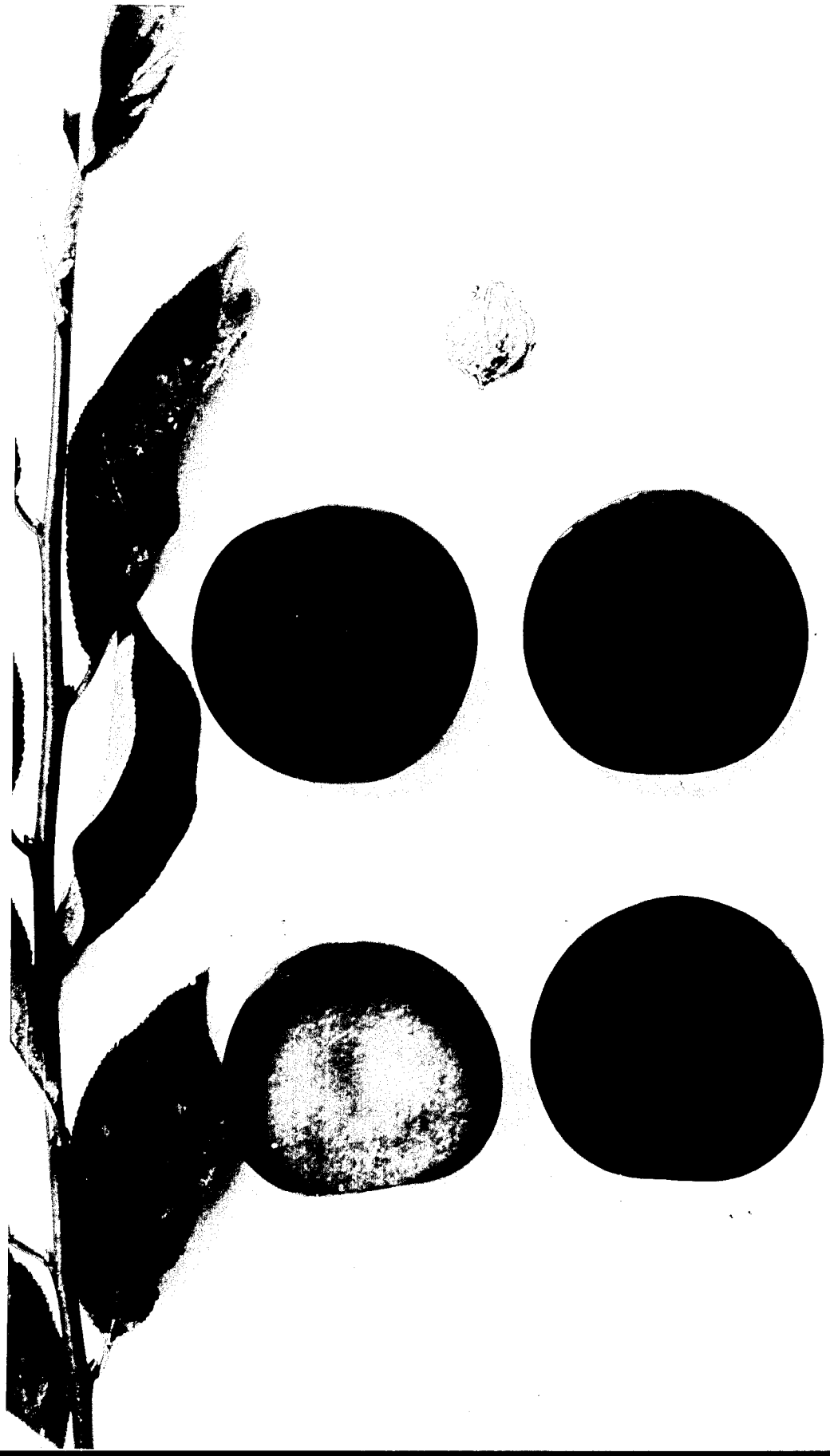

* * * * *